(12) United States Patent
Qin

(10) Patent No.: US 7,008,568 B2
(45) Date of Patent: Mar. 7, 2006

(54) PHOTOCHROMIC NAPHTHOPYRAN COMPOUNDS: COMPOSITIONS AND ARTICLES CONTAINING THOSE NAPHTHOPYRAN COMPOUNDS

(75) Inventor: Xuzhi Qin, Hacienda Heights, CA (US)

(73) Assignee: Vision-Ease Lens, Inc., Ramsey, MN (US)

(*) Notice: Subject to any disclaimer, the term of this patent is extended or adjusted under 35 U.S.C. 154(b) by 0 days.

(21) Appl. No.: 10/038,350

(22) Filed: Nov. 20, 2001

(65) Prior Publication Data

US 2003/0146419 A1   Aug. 7, 2003

(51) Int. Cl.
G02B 5/23 (2006.01)
C07D 311/78 (2006.01)
C07D 471/00 (2006.01)

(52) U.S. Cl. ............. 252/586; 549/381; 549/330; 549/331; 549/354; 546/41; 548/417; 540/576

(58) Field of Classification Search ......... 252/586; 549/381, 330, 331, 354, 12, 24, 25, 41; 546/41; 548/417; 540/576
See application file for complete search history.

(56) References Cited

U.S. PATENT DOCUMENTS

| | | | |
|---|---|---|---|
| 3,567,605 A | 3/1971 | Becker | 204/158 |
| 3,627,690 A | 12/1971 | Casella et al. | 252/300 |
| 4,826,977 A | 5/1989 | Heller et al. | 544/70 |
| 5,200,116 A | 4/1993 | Heller | 252/586 |
| 5,238,981 A | 8/1993 | Knowles | 524/110 |
| 5,411,679 A | 5/1995 | Kumar | 252/586 |
| 5,429,744 A | 7/1995 | Hagqvist | 210/493.1 |
| 5,451,344 A | 9/1995 | Knowles et al. | 252/586 |
| 5,458,814 A | 10/1995 | Kumar et al. | 252/586 |
| 5,645,767 A | 7/1997 | Van Gemert | 252/586 |
| 5,651,923 A | 7/1997 | Kumar et al. | 252/586 |
| 5,698,141 A | 12/1997 | Kumar | 252/586 |
| 5,723,072 A * | 3/1998 | Kumar | 252/586 |
| 5,811,503 A * | 9/1998 | Herold et al. | 526/323.2 |
| 6,018,059 A | 1/2000 | Chan | 549/382 |
| 6,146,554 A | 11/2000 | Melzig et al. | 252/586 |
| 6,348,604 B1 | 2/2002 | Nelson et al. | 549/389 |
| 6,555,028 B1 * | 4/2003 | Walters et al. | 252/586 |
| 6,660,727 B1 * | 12/2003 | Mann et al. | 514/183 |
| 6,736,998 B1 * | 5/2004 | Petrovskaia et al. | 252/586 |
| 6,858,732 B1 * | 2/2005 | Qin et al. | 546/41 |

FOREIGN PATENT DOCUMENTS

| | | |
|---|---|---|
| WO | WO 95/05382 | 2/1995 |
| WO | WO 96/14596 | 5/1996 |
| WO | WO 97/21698 | 6/1997 |
| WO | WO 01/60811 | 8/2001 |

\* cited by examiner

Primary Examiner—Philip C. Tucker
(74) Attorney, Agent, or Firm—Mark A. Litman & Associates, P.A.

(57) ABSTRACT

A photochromic naphthopyran displays good color distribution when the naphthopyran has a central nucleus of the formula:

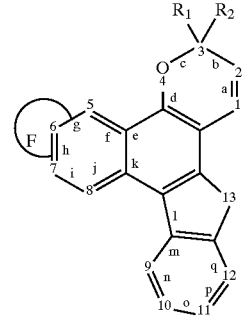

wherein F is a 5-member, 6-member, or 7-member heterocyclic ring group having only one heteroatom, the heteroatom selected from the group consisting of oxygen, sulfur, and nitrogen, the 2,3 or 3,2 positions of the heterocyclic ring fused to the g, h, or i side;
$R_1$ and $R_2$ are the atoms or groups providing photochromic properties to the naphthopyran.

14 Claims, No Drawings

PHOTOCHROMIC NAPHTHOPYRAN COMPOUNDS: COMPOSITIONS AND ARTICLES CONTAINING THOSE NAPHTHOPYRAN COMPOUNDS

BACKGROUND OF THE INVENTION

1. Field of the Invention

The present invention relates to novel naphthopyran-type compounds that have, in particular, photochromic properties. The invention also relates to photochromic compositions and photochromic ophthalmic articles (goggles, lenses and eye-shields, for example) that contain these naphthopyrans. The invention also covers the preparation of these novel naphthopyrans. The photochromic compounds are capable of changing color under the influence of a first poly- or mono-chromatic light (UV for example) and of returning to their initial color when the luminous irradiation ceases, or under the influence of temperature and/or poly- or mono-chromatic light different from the first light. The invention particularly relates to indenonaphthopyrans having a heterocyclic group fused to the naphthalene core.

2. Background of the Art

Photochromism generally concerns the ability of a compound to reversibly change color under different light conditions. One particular type of photochromic phenomenon concerns the reversible change in color of a compound from an original color to a different color when the compound is exposed to a source of ultraviolet radiation, such as solar radiation or light radiated from a mercury or xenon lamp. The photochromic compound fades to the original color within a period of time after the photochromic compound is isolated from the ultraviolet radiation, such as by placing the compound in a dark room.

Photochromic compounds find applications in various fields, such as for the manufacture of ophthalmic lenses, contact lenses, solar protection glasses, goggles, sun screens, filters, camera optics, photographic apparatus optics or other optical devices and observation devices, glazing, decorative objects, currency elements and even for information storage by optical inscription (coding). For example, photochromic compounds, such as naphthopyrans, are incorporated into plastic ophthalmic lenses to effect color changes in the lenses when the lenses are exposed to particular lighting conditions. Additionally, different photochromic compounds may be blended together to create a color effect that is different from respective color effects of the individual photochromic compounds. As an example, a first photochromic compound that turns orange or red when activated by light and a second photochromic compound that turns blue when activated by light may be blended together to form a photochromic mixture that produces a shade of gray when activated by light.

In the field of ophthalmic optics, and in particular the field of spectacles, a photochromic lens that comprises one or more photochromic compounds is usually required to have:

- a high transmission level in the visible region in the absence of ultraviolet radiation,
- a low transmission (high colorability) under solar irradiation (especially with ultraviolet exposure),
- desired coloration and discoloration kinetics, e.g., high sensitivity to irradiation and fast bleaching,
- a high solubility in hosting materials,
- a tint acceptable to the consumer (gray or brown preferably) with the chosen tint maintained during the coloration and the discoloration of the lens,
- a maintenance of the performance and properties, within a temperature range of 0–40° C.,
- a significant durability, since these objectives sought after are used in sophisticated corrective lenses and are therefore expensive.

These lens characteristics are primarily determined by the active photochromic compounds. These compounds must furthermore be compatible with the organic or inorganic support that constitutes the lens.

Moreover, it is to be noted that obtaining a neutral, gray or brown tint may necessitate the use of at least two photochromes of different colors, i.e., two separate compounds having distinct maximal absorption wavelengths in the visible region of the electromagnetic spectrum. The use of combinations of photochromic compounds imposes other requirements on both the individual photochromic compounds and the groups of photochromic compounds. In particular, the coloration and discoloration kinetics of the (two or more) combined active photochromic compounds must be essentially identical. The same applies for their stability with time, and also for their compatibility with a single plastic or inorganic support.

Amongst the numerous photochromic compounds described in the prior art, benzopyrans or naphthopyrans are described in patents or patent applications U.S. Pat. Nos. 3,567,605; 3,627,690; 4,826,977; 5,200,116; 5,238,981; 5,411,679; 5,429,744; 5,451,344; 5,458,814; 5,651,923; 5,645,767; 5,698,141; WO-A-95 05382; WO-A-96-14596; WO-A-97 21698 which are of the reduced formula below:

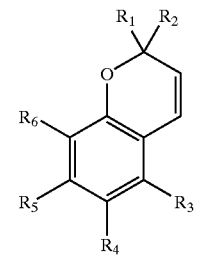

Specifically, U.S. Pat. Nos. 5,645,767 and 5,955,520 describe photochromic inden[2,1-f]naphtho[1,2-b]pyrans showing activated colors ranging from orange to blue-gray:

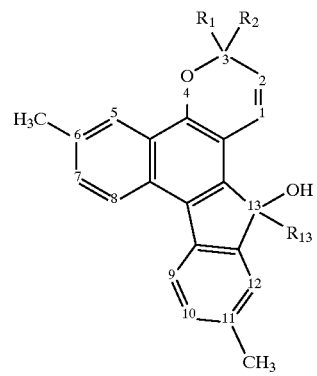

U.S. Pat. No. 5,645,767
U.S. Pat. No. 5,955,520

Those photochromic materials are characterized by a major absorption of visible light in the 580–620 nm range coupled with a minor absorption in the 420–500 nm range.

U.S. Pat. Nos. 5,698,141 and 5,723,072 describe naphthopyrans having benzofuran groups fused to the naphthalene core of the indeno-naphthopyran:

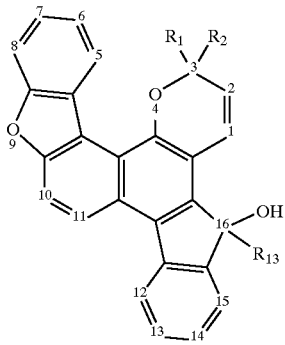

U.S. Pat. No. 5,698,141
U.S. Pat. No. 5,723,072

U.S. Pat. No. 6,146,554 discloses indeno-naphthopyrans having a green activated color by fusing a benzene ring to the indene core:

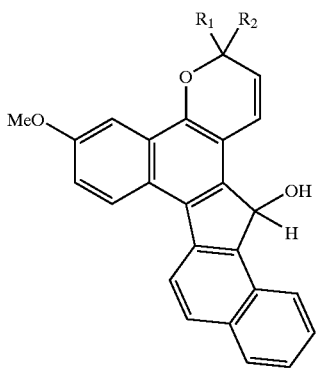

U.S. Pat. No. 6,146,554

The green color is perceived when having a major absorption of visible light in the 580–620 nm range coupled with another major absorption of roughly equal intensity in 400–480 nm range.

U.S. Pat. No. 6,225,466 discloses indeno-naphthopyrans having a spiro-ring attached to the indene core.

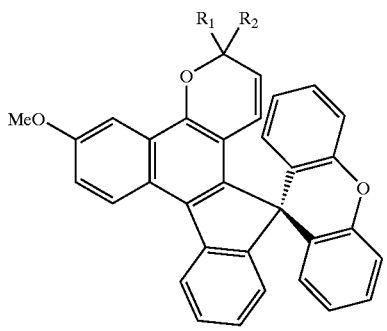

U.S. Pat. No. 6,225,466

More specifically, U.S. Pat. No. 6,296,785 describes indeno[2,1-f]naphtho[1,2-b]pyrans having alkoxy substituents specifically at 6- and 7-position:

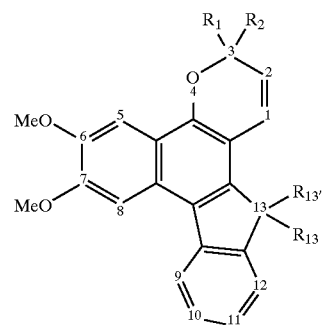

U.S. Pat. No. 6,296,785

The compounds have two absorption bands in the visible spectrum. Band A, which occurs in 420–500 nm region, is generally of greater intensity than Band B, which occurs in 500–650 nm region. Various other substituent groups are defined, in terms of type and position, in the patent and encompass a wide, art-accepted range of combinations of substituents intended to control the wavelength and/or intensity of the visible absorbance bands. The patent claims that the use of certain individual compounds in the invention eliminates the need for combining two or more compounds to obtain neutral colors such as gray or brown. In reality, even if these compounds really do have one or more of the basic properties sought after, such as a high transmission in the absence of ultraviolets and a high colorability under solar irradiation, none of the compounds described hitherto have the complete combination of properties necessary for the production of satisfactory articles. In particular, none of these compounds is intrinsically gray that, for photochromic materials having two major absorption bands in the visible spectrum range, requires roughly equal intensity for the two bands while they are limited in relatively narrow ranges of wavelength. To have roughly equal intensity bands, compounds within the scope of the patent need a strong electron donor group, such as morpholino, at the p-position of the 3-position phenyl. At the same time, this will bathochromically shift the peak of Band A to a wavelength greater than 480 nm, and Band B greater than 590 nm. Consequently, green or purple-blue color is observed as in U.S. Pat. No. 6,146,554. The necessity of using an additional photochromes in order to obtain a neutral gray does subsist.

It is the merit of the applicant to have found, surprisingly, that a fused saturated heterocyclic ring, particularly oxygen heterocyclic, to the 6,7- or 6,5- or 8,7-positions of the indeno-naphthalene core provided desirable photochromic compounds. The two absorption peaks exhibited bye these compound are not only distinct in the 430–460 nm range and 550–580 nm range but also of roughly equal intensity. By selecting proper substituents on the other portion of the naphthopyran, certain compounds of the present invention can eliminates the need of two or more photochromic dyes in order to have a neutral gray activated color. In addition, these compounds have demonstrated high sensitivity to solar radiation.

SUMMARY OF THE INVENTION

A novel family of molecules is described having particularly advantageous photochromic properties, such as, two distinct and equal intensity absorption bands in the 430–460 nm range and 550–580 nm range of the visible spectrum. This novel type of compounds either exhibits acceptable purple-gray to green-gray tint by itself or blends well in association with yellow photochromes to give brown tint.

According to a first aspect of the invention is described a naphthopyran having a central nucleus of the formula:

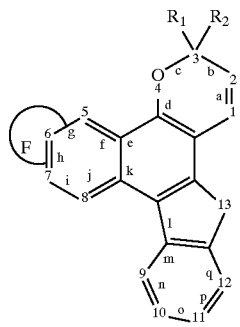

wherein F is a 5- to 7-member heterocyclic ring group with one heteroatom selected from oxygen, sulfur, and nitrogen, its 2,3 or 3,2 positions fused to the g, h, or i side, and preferably only a single oxygen or single sulfur atom;

$R_1$ and $R_2$ are the atoms or groups providing photochromic properties to the naphthopyran.

This naphthopyran may preferably have RI is selected from the group consisting of a hydrogen, a linear or branched alkyl group of 1 to 12 carbon atoms, a cycloalkyl group of 3 to 12 carbon atoms, an aryl group of 6 to 24 ring carbon atoms or a heteroaryl group of 4 to 24 carbon atoms and at least one hetero ring atom selected from sulfur, oxygen and nitrogen; and wherein $R_1$ and $R_2$ together form an adamantyl, norbornyl, fluorenylidene, di(C1–C6)alkylanthracenylidene or spiro(C5–C6)cycloalkylanthracenylidene group.

Another aspect of the invention is a naphthopyran having the central nucleus of

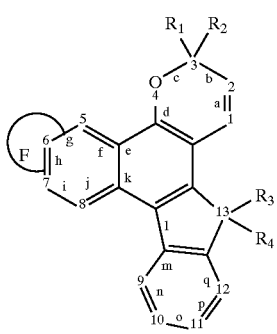

the formula:
wherein F is a 5- to 7-member heterocyclic ring group with one heteroatom selected from oxygen, sulfur, and nitrogen, its 2,3- or 3,2-positions fused to the g, h, or i side;

$R_1$ and $R_2$ are the atoms or groups necessary to provide photochromic properties to the naphthopyran, and $R_3$ and R4 are the atoms or groups providing acceptable fading kinetics of the photochromes, is selected from the group consisting of:

hydrogen, hydroxy, a halogen, a linear or branched alkyl group of 1 to 12 carbon atoms, cycloalkyl group of 3 to 12 carbon atoms, linear or branched alkoxy group of 1 to 12 carbon atoms, linear or branched alkenyl or alkynyl group of 1–12 carbon atoms, linear or branched alkenyloxy or alkynyloxy group of 1–12 carbon atoms; or unsubstituted or mono- or multi-substituted aryl or heteroaryl group, said substituents selected from halogen, C1–C6 alkyl, C1–C6 alkoxy; or aralkyl or heteroaralkyl group, the alkyl group, which is linear or branched, of 1 to 4 carbon atoms, and the aryl or heteroaryl group optionally substituted with groups selected from halogen, C1–C6 alkyl, and C1–C6 alkoxy.

According to another aspect of the present invention, naphthopyran compounds of the following formula (I) are described and enabled:

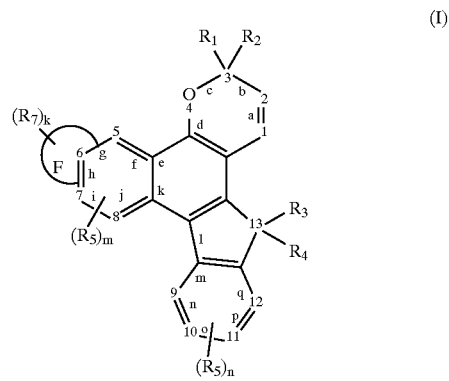

(I)

in which:
F is a 5- to 7-member heterocyclic ring group with one heteroatom selected from oxygen, sulfur, and nitrogen, with or without substitutions. Its 2,3 or 3,2 positions fused to the g, h, or i side of the naphthopyran as identified in Formula (I);

$R_1$ and $R_2$, for example, may independently represent:
a hydrogen,
a linear or branched alkyl group which comprises 1 to 12 carbon atoms (with or without substitution),
a cycloalkyl group which comprises 3 to 12 carbon atoms,
an aryl or heteroaryl group which comprises in its basic structure (that is, in its ring atoms, the rings comprising 5, 6 or 7 atoms) 6 to 24 carbon atoms or 4 to 24 carbon atoms respectively and at least one heteroatom selected from sulfur, oxygen and nitrogen; the basic structure being optionally substituted with at least one substituent selected from:
a halogen atom (e.g., fluorine, chlorine and bromine),
a hydroxy group,
a linear or branched alkyl group comprising 1 to 12 carbon atoms, a linear or branched alkoxy group comprising 1 to 12 carbon atoms, a haloalkyl or haloalkoxy group corresponding to the (C$_1$–C$_{12}$) alkyl or alkoxy groups above respectively which are substituted with at least one halogen atom, and notably a fluoroalkyl group of this type, a linear or branched alkenyl group comprising 2 to 12 carbon atoms, and notably a vinyl group or an allyl group, an amino group:

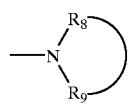

in which $R_8$ and $R_9$, which are the same or different, independently representing a hydrogen, a linear, branched, or cyclic alkyl group comprising 1 to 6 carbon atoms, an aryl or heteroaryl group, or representing (together with the nitrogen atom to which they are bound) a 5- to 7-membered ring which can comprise at least one other heteroatom selected from oxygen, sulfur and nitrogen, said nitrogen being optionally substituted with an RIO group, which is a linear or branched alkyl group comprising 1 to 6 carbon atoms, a phenyl, a benzyl, or a naphthyl, a methacryloyl group or an acryloyl group, an aralkyl or heteroaralkyl group, the alkyl part of which is linear or branched, comprising 1 to 4 carbon atoms and the aryl and heteroaryl groups having the definitions given above, or the two substituents R1 and R2 together forming ring group such as those represented by an adamantyl, norbornyl, fluorenylidene, 5,5- or 10,10-di(C1–C6)alkylanthracenylidene, 5 (or 10)-(C1–C6)alkyl-5 (or 10)-OH (or OR$_{10}$)anthracenylidene or spiro(C5–C6)cycloalkylanthracenylidene ring group; said ring group being optionally substituted with at least one of the substituents listed above in the definitions for $R_1$, $R_2$; said ring group being optionally substituted with-two adjacent groups that form a 5- to 6-member aromatic or non-aromatic ring which can comprise at least one heteroatom selected from oxygen, sulfur, and nitrogen.

$R_3$ and R4 are identical or different and they represent, independently, a hydrogen atom, a hydroxy group, a halogen atom (e.g., fluorine, chlorine and bromine), a linear, branched, or cyclic C1–C6 alkyl, alkenyl, or alkynyl group, a linear, branched, or cyclic C1–C6 alkoxy or alkenoxy group, an amino group:

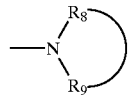

in which $R_8$ and $R_9$ are defined as in $R_1$ and $R_2$, an optionally substituted aryl or heteroaryl group selected from phenyl, naphthyl, phenanthryl, pyrenyl, quinolyl, isoquinolyl, benzofuranyl, thienyl, benzothienyl, dibenzofuranyl, dibenzothienyl, carbazolyl, indolyl, said substituents being selected from the group consisting of chloro, fluoro, C1–C6 alkyl and C1–C6 alkoxy, a mono-substituted phenyl having a substituent at the para position that is a linking group,—(CH$_2$)$_t$— or —O—(CH$_2$)$_t$—, wherein t is the integer 1, 2, 3, 4, 5 or 6, connected to an aryl group, e.g. phenyl or naphthyl, which is a member of another photochromic naphthopyran, such as naphtho[2,1-b]pyran or naphtho[1,2-b]pyran, an aralkyl or heteroaralkyl group, the alkyl part of which is linear or branched, comprising 1 to 4 carbon atoms and the aryl and heteroaryl groups having the definitions given supra, a —C(O)R$_{11}$, —OC(O)R$_{11}$, or COOR$_{11}$ group, wherein $R_{11}$ is hydrogen, hydroxy, linear or branched C1–C6 alkyl, linear or branched C1–C6 alkoxy, phenyl, mono-substituted phenyl, naphthyl, mono-substituted naphthyl, amino, mono(C1–C6) alkylamino or di(C1–C6)alkylamino, e.g., N,N-dimethyl amino, N-methyl-N-propyl amino, etc., morpholino, piperidino or pyrrolidyl, said amino substituents being selected from the group consisting of C1–C6 alkyl, phenyl, benzyl and naphthyl, and said benzyl and phenyl substituents being C1–C6 alkyl or C1–C6 alkoxy, a group —OR$_{12}$, wherein R$_{12}$ is a C1–C6 acyl, an aralkyl or heteroaralkyl group with a C1–C3 alkyl portion and an aromatic portion defined supra in $R_1$ and $R_2$, a (C3–C7)cycloalkyl group, a (C2–C4)alkyl group optionally substituted with C1–C6 alkoxy, fluoro, chloro, or R$_{12}$ is the group, —CH(R$_{13}$)R$_{14}$, wherein R$_{13}$ is hydrogen or C1–C3 alkyl and R$_{14}$ is —CN, —CF$_3$, or —COOR$_{15}$, wherein R$_{15}$ is hydrogen or linear, branched, or cyclic alkyl, aralkyl or heteroaralkyl, said aryl substituted with alkyl or alkoxy, a group —CH(R$_{16}$)$_2$ wherein R$_{16}$ is —CN or —COOR$_{15}$, a group —CH(R$_{15}$)R$_{17}$, wherein R$_{17}$ is —COOR$_{11}$, —C(O)R$_{18}$ or —CH$_2$ OR$_{19}$, wherein R$_{18}$ is hydrogen, linear, branched, or cyclo-alkyl, the unsubstituted, or multi-substituted aryl groups phenyl or naphthyl, amino group of formula

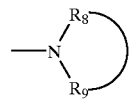

as defined in $R_1$ and $R_2$, R$_{19}$ is hydrogen, —C(O)R$_{11}$, alkyl, alkoxyalkyl, phenylalkyl, mono-alkoxy substituted phenyl-alkyl, or the unsubstituted, mono- or di-substituted aryl groups phenyl or naphthyl, each of said aryl group substituents being C1–C6 alkyl or C1–C6 alkoxy, a polyether, polyamide, polycarbonate, polycarbamate, polyurea, polyester residue, or a group ended by a polymerizable residue.

Alternatively, $R_3$ and $R_4$ may together form a 3- to 7-member optionally substituted spiro-cyclic ring which can comprise at least one heteroatom selected from oxygen, sulfur, and nitrogen, and/or at least one substituent selected from the group consisting of a C1 to C6 alkyl group which is linear or branched, a C1 to C6 alkoxy group which is linear or branched, and an amine group of formula

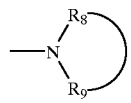

as defined in $R_1$ and $R_2$ for amine groups. The spiro-ring may be annelated with one or two aromatic groups. Examples of the spiro-carbocyclic ring substituents include spirofluoreno, spirocyclopropyl, spirocyclobutyl, spirocyclopentyl, spirocyclohexyl, spiroindan-1-yl, spiroindan-2-yl, etc. Examples of the spiro-heterocyclic group include spiroxantheno and compounds which may be represented by the expression (—O—(C2–C5 alkanediyl)—O—), e.g., spiro-1,3-dioxolane-2, spiro-1,3-dioxane-2, etc. or spirolactones such as butyrolactone, propiolactone etc.

In the definitions of $R_3$ and $R_4$, like substituents have like meanings.

$R_5$ and $R_6$ may independently represent:
- a hydrogen,
- a halogen, and notably fluorine, chlorine or bromine,
- a linear or branched alkyl group which comprises 1 to 12 carbon atoms (advantageously 1 to 6 carbon atoms),
- a cycloalkyl group comprising 3 to 12 carbon atoms,
- a linear or branched alkoxy group comprising 1 to 12 carbon atoms (most advantageously 1 to 6 carbon atoms),
- a haloalkyl, halocycloalkyl, or haloalkoxy group corresponding to the alkyl, cycloalkyl, alkoxy groups above respectively, which are substituted with at least one halogen atom, notably selected from fluorine, chlorine and bromine,
- a linear or branched alkenyl or alkynyl group comprising 1–12 carbon atoms, preferably a vinyl or allyl group,
- a linear or branched alkenoxy or alkynoxy group comprising 1–12 carbon atoms, preferably an allyloxy group,
- an aryl or heteroaryl group having the same definition as that given above for aryl or heteroaryl groups within the definitions of $R_1$, $R_2$,
- an aralkyl or heteroaralkyl group, the alkyl group, which is linear or branched, comprising 1 to 4 carbon atoms, and the aryl and heteroaryl groups having the same definitions as those given above for $R_1$, $R_2$,
- an amine or amide group: —$NH_2$, —$NHR_8$, —$CONH_2$, —$CONHR_8$,

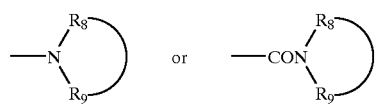

$R_8$, and $R_9$ having their respective definitions given above for the amine substituents of the values $R_1$, $R_2$, a —$C(R_{15})_2R_{11}$, —$OCOR_{15}$, or —$COOR_{15}$ group, wherein $R_{11}$ and $R_{15}$ are defined supra in $R_3$ and $R_4$, a methacryloyl group or an acryloyl group,

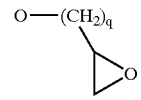

an epoxy group having the formula,
in which q=1, 2 or 3,

When n is 2, two adjacent $R_5$ together form a 5- to 7-member aromatic or non-aromatic ring which can comprise at least one heteroatom selected from oxygen, sulfur, and nitrogen, and/or at least one substituent selected from the group consisting of a C1 to C6 alkyl group which is linear, branched, or cyclic, a C1 to C6 alkoxy group which is linear or branched, and an amine group of formula —$NH_2$, $NHR_8$, or

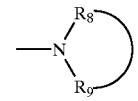

as defined in $R_1$ and $R_2$ for amine groups, said aromatic or non-aromatic ring can be optionally annelated with a benzene group, a polyether, polyamide, polycarbonate, polycarbamate, polyurea or polyester residue, or a group with polymerizable residue, n is an integer from 0 to 4, and m is an integer from 0 to 2;

each $R_7$ group can be the same or different, independently representing
- a hydrogen,
- a halogen, and notably fluorine, chlorine or bromine,
- a linear or branched alkyl group which comprises 1 to 12 carbon atoms (advantageously 1 to 6 carbon atoms),
- a cycloalkyl group comprising 3 to 12 carbon atoms,
- a linear or branched alkoxy group comprising 1 to 12 carbon atoms (most advantageously 1 to 6 carbon atoms),
- a haloalkyl, halocycloalkyl, or haloalkoxy group corresponding to the alkyl, cycloalkyl, alkoxy groups above respectively, which are substituted with at least one halogen atom, notably selected from fluorine, chlorine and bromine,
- a linear or branched alkenyl or alkynyl group comprising 1–12 carbon atoms, preferably a vinyl or allyl group,
- a linear or branched alkenoxy or alkynoxy group comprising 1–12 carbon atoms, preferably an allyloxy group,
- two of the $R_7$ groups, which are adjacent or bonded to the same carbon atom in the group F, form a 5- to 7-membered non-aromatic ring which can comprise at least one heteroatom selected from the group consisting of oxygen, sulfur, and nitrogen, k is an integer from 0 to 4.

The terms "group" and "central nucleus" have established meanings according to the practice of the present invention. Where the term "group" is used, the chemical unit described is intended to include and allow for substituents consistent with the primary chemical unit. For example, where the term alkyl group is used, that term is intended to include classic alkyl materials such as methyl, ethyl, propyl, butyl, hexyl, octyl, iso-octyl, dodecyl, cyclohexyl and the like, and is also intended to include alkyl units with substitution thereon consistent with the underlying nature of an alkyl unit, such as hydroxymethyl, bromoethyl, dichloropropyl, 1,2,3,4-tetrachlorobutyl, omega-cyanohexyl and the like. When the term "alkyl moiety" is used, no substitution is allowed.

The terminology of a central nucleus of a provided formula has a similar meaning. The term indicates that the formula, even though atoms are shown in the formula, may be substituted with any chemical units as long as the underlying bond structure of the formula is not altered. For example, where the term a central nucleus of the formula

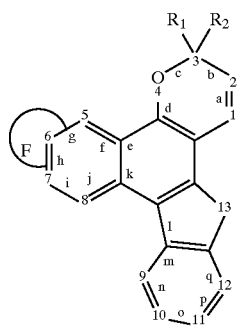

is used, there may be any substitution at such positions as 1, 2, 5, 6, 7, 8, 9, 10, 11, 12, or 13 as long as the structure of F is not destroyed and the bond structure shown (e.g., the double bonds) are not converted to single bonds (e.g., by attempting to provide two substituents at the 6-position, which would require elimination of the double bond between positions 5 and 6. Where the term a compound of the formula is used, except for description of the term 'group' in definitions, no unspecified substitution is allowed.

Where the term 'group' or 'central nucleus' is used in the practice of the present invention, those terms refer to the capability of the structure to have substitution or not on the chemical unit or not. The term 'group' refers to any chemical structure, while the term 'central nucleus' refers specifically to a ring structure as the core chemical moiety. For example, an 'alkyl group' includes unsubstituted n-alkyl, iso-alkyl, methyl ethyl, octyl, iso-octyl, docecyl, and the like, and substituted alkyl such as hydroxymethyl, 1-chloroethyl, 2-cyano-butyl, 3-ethyl-4-hexyl, omega-carboxy-pentyl, and the like. Where the term 'moiety' is used, as in the term alkyl moiety is used, that term refers to only unsubstituted chemical units. Similarly, where the term 'central nucleus' is used, such as in the central nucleus of a naphthyl, any substituent may be present on the central nucleus of the naphthyl group, such as 1-methyl-, 2-chloro-, 2,4-dimethoxy-, 2,2'-dimethoxy-, and the like. Where the term having a structure of the specific formula is used, no substitution is allowed beyond that of the described formula.

Among the substituents that can be considered for the compounds of formula (I) according to the invention, groups should be considered that comprise and/or form at least one function which can be polymerized and/or crosslinked, which group are preferably selected from the following list: alkenyl, advantageously vinyl, methacryloyl, acryloyl, acryloxyalkyl, methacryloxyalkyl or epoxy.

Thus, the photochromic compounds according to the invention can be monomers, of different types or not, that can react with each other or with other comonomers to form homopolymers and/or copolymers that bear a photochromic functionality and possess mechanical properties of macromolecules. It follows that one of the objects of the present invention consists of these homopolymers or copolymers comprising (co)monomers and/or of crosslinked compounds, that, at least in part, consist of photochromic compounds (I) according to the invention.

In the same general concept, the above-mentioned compounds (I) can be crosslinking agents that have one or more reactive functions capable of allowing the formation of bridges between chains of polymers of photochromic nature or not. The crosslinked compounds that can be obtained in this manner also are a part of the present invention.

Amongst such compounds according to formula (I), preferred photochromic are those which have the formula (Ia), (Ib), and (Ic) below:

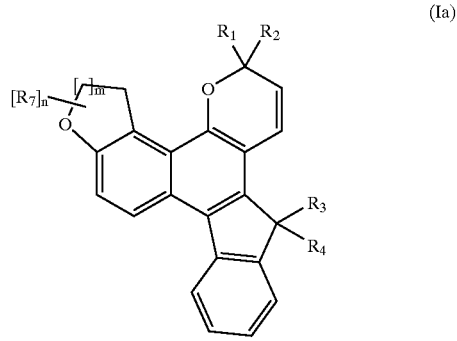

(Ia)

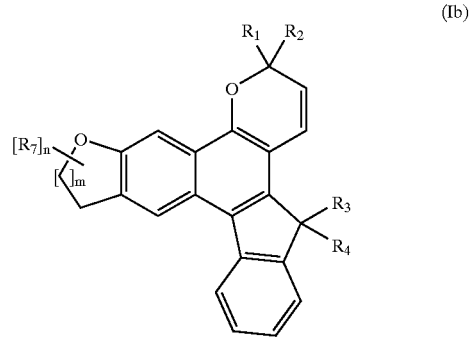

(Ib)

-continued

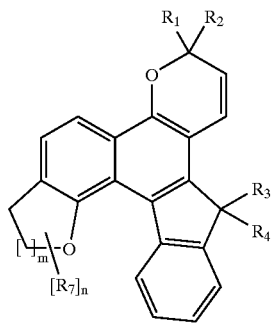

(Ic)

in which:

m is an integer 1 or 2,

R₁ and/or R₂, independently represent optionally substituted aryl or heteroaryl groups the basic structure of which is selected from those of phenyl, naphthyl, biphenyl, pyridyl, furyl, benzofuryl, dibenzofuryl, N—($C_1$–$C_6$)alkylcarbazole, thienyl, benzothienyl, dibenzothienyl, julolidinyl groups; R₁ and/or R₂ advantageously Representing a para-substituted phenyl group, said substituents are selected preferably from alkexy, dialkylamino, diarylamino, or R₁ and R₂ together form an adamantyl group or norbornyl group or anthrasenylidene group;

R₃ and R₄ are the same or different, and may represent independently a hydrogen, a hydroxy, a halogen, a linear, branched, or cyclic alkyl group that comprises 1 to 6 carbon atoms, a —OR₂₀ group, wherein R₂₀ is (C1–C3)alkyl, phenyl (C1–C3)alkyl, mono(C1–C3)alkylphenyl(C1–C3)alkyl, mono(C1–C3)alkoxyphenyl(C1–C3)alkyl, (C1–C3)alkoxy(C2–C4)alkyl, fluoro(C1–C3)alkyl, or chloro(C1–C3)alkyl, an optionally substituted phenyl or benzyl group, said substituents being mono, di-, or tri-, and selected from group R₂₀, a —C(R₂₁)₂X group, wherein X is hydroxy, alkoxy, benzoyloxy, C1–C6 acyloxy, an ester group: COOR₁₁, an amine or amide group: —NH₂, —NHR₈, —N(R₈)₂, —CONH₂, —CONHR₈, —CON(R₈)₂, R₂₁ is hydrogen, C1–C6 alkyl, phenyl or naphthyl with C1–C6 alkyl or C1–C6 alkoxy substituents, a polyether or polyurea residue, or R₃ and R₄ together form a 5- to 7-member optionally substituted spiro-cyclic ring which can comprise at least one heteroatom selected from oxygen, sulfur, and nitrogen, and/or at least one substituent selected from the group consisting of a C1 to C6 alkyl group which is linear or branched, a C1 to C6 alkoxy group which is linear or branched, and an amine group of formula —NH₂, NHR₈, or

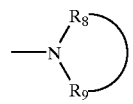

as defined in R, and R2 for amine groups. The spiro-ring may be annelated with one or two benzene groups.

R₇, which are identical or different, represent, independently a hydrogen, a linear or branched alkyl group which comprises 1 to 6 carbon atoms, a cycloalkyl group comprising 3 to 7 carbon atoms, a linear or branched alkoxy group comprising 1 to 6 carbon atoms, a haloalkyl, halocycloalkyl, or haloalkoxy group corresponding to the alkyl, cycloalkyl, alkoxy groups above respectively, which are substituted with at least one halogen atom, notably selected from fluorine, chlorine and bromine, a linear or branched alkenyl or alkynyl group comprising 1–12 carbon atoms, preferably a vinyl or allyl group, a linear or branched alkenoxy or alkynoxy group comprising 1–12 carbon atoms, preferably an allyloxy group, n is an integer from 0 to 2.

These compounds present particularly advantageous photochromic properties, such as, having strong coloration ability with two distinct, equal intensity absorption bands in the visible range. These compounds are also preferably stable and compatible with matrices made of at least one organic polymer or mineral material (e.g., inert inorganic binder), both in the form included in the matrix and in the form of a coating.

In a solution or in the polymer matrix, the compounds according to the invention are colorless or slightly colored in the initial state and they rapidly develop an intense coloration under UV light (365 nm) or a luminous source of the solar type. They recover to their initial color at an acceptable rate when the irradiation stops.

General Synthetic Procedure for Preparation of the Compounds

The compounds of the invention can be obtained by the condensation of a derivative of 1-naphthol that is suitably substituted and a derivative of propargyl alcohol. The condensation can be carried out in organic solvents, particularly non-polar solvents such as toluene, xylene or tetrahydrofuran and, optionally, in the presence of a catalyst, acid catalysts, and especially acid catalysts such as fluorinated organic acid catalysts, p-toluenesulfonic acid, chloroacetic acid or acid aluminic acid):

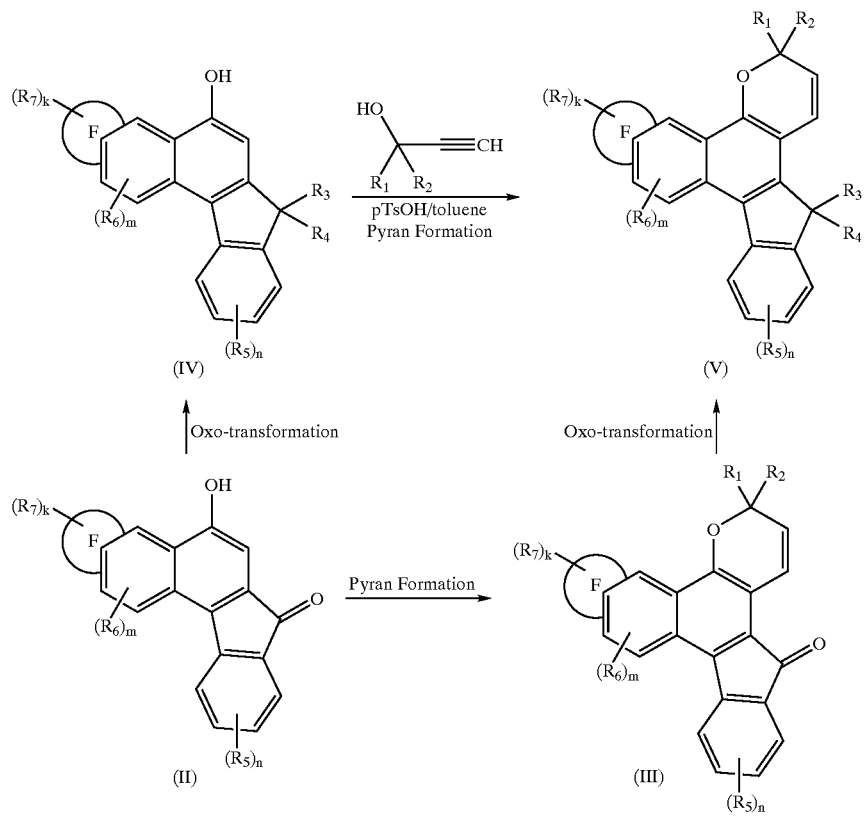

The synthetic routes to naphthopyrans (V) from proper derivatives of 1-naphthol such as (III) and (IV) are classical and have been described in the above-mentioned references of the prior art. The propargyl alcohols are either commercially available or easily synthesized by the reaction of lithium acetylide or ethynyl (magnesium bromide) with the corresponding ketones $R_1C(O)R_2$. The ketones are also either commercially available or easily synthesized by the classical methods, for example, the Friedel-Crafts reaction from an acid chloride.

The oxo-transformation to $R_3$ and $R_4$ can be done either before the pyran formation or after the pyran formation. The transformations to variety of different groups, including spiro-cyclic groups, are achieved by methods familiar to ones in the art. Examples can be found in literature, such as U.S. Pat. Nos. 6,146,554, 6,225,466, and 6,296,785.

The 1-naphthol derivatives (II) and (IV) are obtained by various methods adapted from the literature. Below we illustrate some reactions and give some references on methods that allow the synthesis of the compounds of the invention.

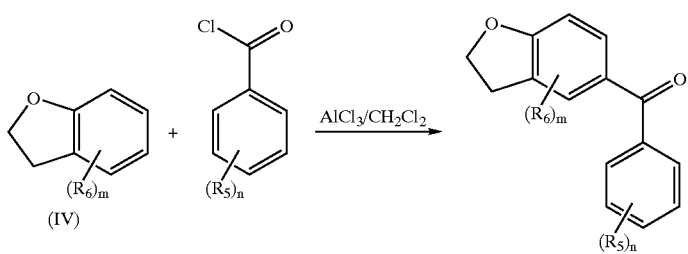

Johnson etal.,
Org. Reaction,
1951, 6, p1

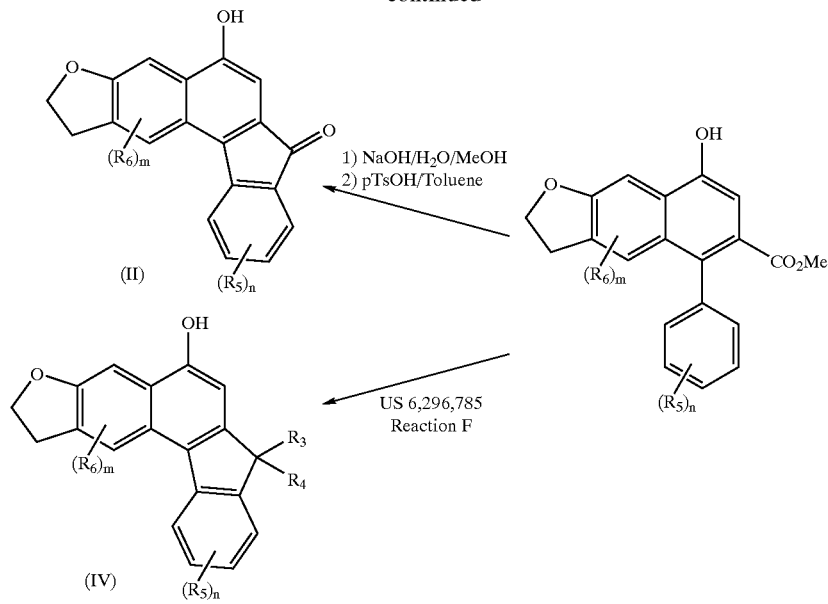

Key: pTsOH: p-toluenesulphonic acid, MeOH: methanol.

The starting compound (IV) can be prepared from the Claisen rearrangement of the corresponding allyl phenyl ether followed by acid-catalyzed cyclization reaction.

Regarding the commercial application of compounds according to the present invention, it should be noted that they can be used as a photochromic material dispersed in the composition of a polymer matrix. They can also be used in solution.

A photochromic solution can be obtained by dissolving the compound in an organic solvent, such as toluene, dichloromethane, tetrahydrofuran or ethanol. The solutions obtained are generally colorless and transparent. When exposed to sunlight, they develop a strong coloration and they recover the color of this state when placed in an environment with lesser exposure to solar radiation or, in other words, when they are no longer exposed to UV radiation. In general, a very low concentration of products (on the order of 0.01–5% by weight or volume) is sufficient to obtain an intense coloration.

The most interesting applications are those in which the photochrome is dispersed uniformly within or on the surface of a polymer, copolymer or mixture of polymers. The implementation methods that can be considered are of a great variety. Among those known to a person skilled in the art, one can cite, for example, diffusion in the (co)polymer, from a suspension or solution of the photochrome, in a silicone oil, in an aliphatic or aromatic hydrocarbon, in a glycol, or from another polymer matrix. Currently the diffusion is carried out at a temperature of 50–200° C. for a duration of 15 minutes to several hours, depending on the nature of th polymer matrix. Another implementation technique consists in mixing the photochrome in a formulation of polymerizable materials, in depositing this mixture on a surface or in a mold and in then carrying out the polymerization. These implementation techniques and others are described in the article by Crano et al. "Spiroxazines and their use in photochromic lenses," published in Applied Photochromic Polymer Systems, Publishers Blackie and Son Ltd., 1992. According to a variant of the invention, it is also possible to consider grafting the photochromes onto (co) polymers. Thus, another aspect of the invention consists of the (co)polymers grafted with at least one of the photochromes described above.

As examples of preferred polymer materials for optical applications of the photochromic compound according to the invention, one can mention the following products: alkyl, cycloalkyl, aryl or arylalkyl poly(mono-, di-, tri-, tetra) acrylate or poly(mono-, di-, tri tetra) methacrylate, optionally halogenated or comprising at least ether and/or ester and/or carbonate and/or carbamate and/or thiocarbamate and/or urea and/or amide group; polystyrene, polycarbonate (e.g., bisphenol A polycarbonate, poly(carbonate of diallyl diethylene glycol), polyepoxy, polyurethane, polythiourethane, polysiloxane, polyacrylonitrile, polyamide, aliphatic or aromatic polyester, vinyl polymers, cellulose acetate, cellulose triacetate, cellulose acetate-propionate or polyvinylbutyral, copolymers of two or more types of monorlers or mixtures of the above-mentioned polymers, preferably polycarbonate-polyurethane, poly(meth)acrylatepolyurethane, polystyrene-poly(meth)acrylate or polystyrene-polyacrylonitrile, advantageously a mixture of polyester and/or polycarbonate or poly(meth)acrylate.

The quantity of photochrome used in various articles depends on the desired degree of darkening. In particular, it is used in a quantity of 0.001–20 wt % of the total weight of the layer in which the photochrome is included. The photochromic compounds according to the invention can be used alone or in a mixture with other products to form a composition that can be in solid or liquid form, for example, in a solution or in a dispersion, as has already been mentioned above. These compositions, which constitute another object of the invention, can comprise one or more compounds (I) according to the invention and other complementary photochromic compounds which allow the attaining of dark colorations, for example, gray or brown, which the public desires in applications such as ophthalmic or sun-protection eyewear. These additional photochromic compounds can be those known to a person skilled in the art and described in the literature, for example, other naphthopyrans, benzopyrans, chromenes (U.S. Pat. Nos. 3,567,605, 5,238,981, World Patent No. 9,422,850, European Patent No. 562,915), spiropyrans or naphthospiropyrans (U.S. Pat. No. 5,238,981) and spiroxazines (CRANO et al., "Applied Photochromic Polymer Systems," Publishers Blackie & Son Ltd., 1992, Chapter 2).

These compositions according to the invention can also comprise:

Non-photochromic dyes allowing the adjustment of the tint, and/or one or more stabilizers, such as, for example, an antioxidant, and/or one or more anti-UV screens, and/or one or more anti[free]radical agents, and/or deactivators that deactivate the states of photochemical excitation.

These additives can enable further improvements in the durability of said compositions.

According to another one of its aspects pertaining to the application of the photochromic compounds (I), the present invention also relates to ophthalmic articles, such as articles of ophthalmic or sun protection eyewear articles, or eye shields comprising at least one compound according to the invention and/or at least one (co)polymer formed, at least in part, of repeating units derived from compounds having formula (I) and/or at least one composition comprising compounds (I) according to the invention, as defined above, and/or at least one matrix, as defined above, made of an organic polymer material or a mineral material or a mineral-organic hybrid material incorporating at least one compound of the invention.

In practice, the articles to which the present invention applies more particularly are photochromic ophthalmic or sun-protection lenses, glass paneling (glasses for buildings, for locomotion devices, automobiles), optical devices, decorative articles, sun-protection articles, information storage, etc.

The present invention will be better understood in the light of the following examples of synthesis and photochromic validation of compounds having the general formula (I). These examples are net intended to be interpreted as limiting the invention, but rather, show specific aspects of the invention within the broad generic scope disclosed.

EXAMPLES

Example 1

Step 1: To a reaction flask containing 2,3-dihydrobenzofuran (13.5 grams) and benzoyl chloride (16.6 grams) in 170 milliliters (mL) of methylene chloride were added anhydrous aluminum chloride (18.0 grams) under nitrogen blanket over 40 minutes. The reaction temperature was controlled at around 25° C. with an ice/water bath. The reaction mixture was stirred at room temperature overnight. The resulting mixture was poured into 150 mL of ice/water and stirred vigorously for 30 minutes. The organic layer was separated, washed with water, dried over magnesium sulfate. The methylene chloride solvent was removed by rotary evaporation to give 25 grams of thick pink oil. It is used 'as is' in the next step.

Step 2: The product from Step 1 (25 g), dimethyl succinate (21.0 g), and potassium t-butoxide (16.5 g) were mixed in 250 ml of toluene. The mixture was refluxed for 2 hours under nitrogen blanket. After it was cooled to room temperature, 200 ml of water was added and mixed well. The aqueous phase was separated, acidified with 5N HCl, and extracted with 3×100 ml of ethyl acetate. The combined extracts were washed once with water, dried over magnesium sulfate. The solvent was remove under reduced pressure to give 40.5 g of honey-like crude half-ester product. It was known that the crude product contains some aliphatic oil contaminants from the ethyl acetate solvent. It is used without purification.

Step 3: The crude half-ester from Step 2 (40 g) was added to reaction flask containing 180 ml of acetic anhydride and 23 g of anhydrous potassium acetate. The mixture was refluxed for 1.5 hours, cooled, filtered. The solid in the filtration funnel was washed thoroughly with ethyl acetate. The combined filtrate was concentrated to just dry under vacuum. The dark solid was re-dissolved in ethyl acetate and washed with water, dried over magnesium sulfate. The organic solution was concentrated under reduced pressure. The residual was subjected to a silica column with ethyl acetate/hexane 1:4 as elutant. Two main portions were obtained: 8.7 g of light yellow solid, and 36 g of light brown thick oil. An NMR spectrum showed the yellow solid to have a structure of (2,3-dihydro-5-phenyl-6-methoxycarbonyl-8-acetoxy-naphtho[2,3-b]furan). The oil portion contains mainly the isomers of the above product.

Step 4: The light yellow solid product from Step 3(8.7 grams) was added to a reaction flask containing 75 mL of water, 25 ml of 5N sodium hydroxide, and 50 mL of methanol. The mixture was refluxed overnight and cooled to give a clear brown solution. It acidified with 5N hydrochloric acid. The precipitate was collected with filtration, and washed with water for 3 times. A beige powder (6.8 g) was obtained after drying the precipitate in a vacuum oven. An NMR spectrum showed the product to have a structure consistent with 2,3-dihydro-5-phenyl-6-carboxyl-8-hydroxy-naphtho[2,3-b]furan.

Step 5: The product from Step 4 (4.8 grams), 20 mL of toluene and 6.0 grams of p-toluenesulfonic acid were added to a reaction flask fitted with a Dean-Stark trap. The resulting mixture was heated to reflux for 5 hours. A deep red solid precipitate formed. The mixture was cooled and 100 ml of water was added. The solid was collected by vacuum filtration, re-dissolved in 500 ml of ethyl acetate, washed with 5% sodium carbonate solution, and thoroughly washed with water. The organic phase was concentrated with rotary evaporation to give a mixture. It was vacuum filtered to yield 3.0 grams of a violet product. An NMR spectrum showed the product to have a structure consistent with 2,3-dihydro-10-oxo-12-hydroxy-indeno[3,2-a]naphtho[2,3-b]furan:

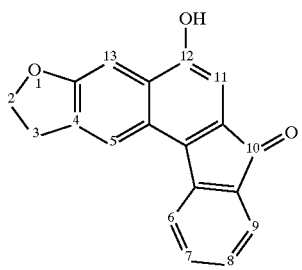

Step 6: The product from Step 5 (0.50 grams) was added to a reaction flask containing 1-(4-methoxyphenyl)-1-phenyl-2-propyn-1-ol (0.86 grams), 50 mL of toluene. After the mixture started to reflux, catalytic amount of p-toluenesulfonic acid was added. The reaction mixture was refluxed overnight, cooled, filtered. The organic filtrate was concentrated by rotary evaporation. The residue was allowed to crystallized overnight, and digested with cold acetone to yield 0.5 grams of red product.

Step 7: The product from Step 6 (0.5 grams) was dissolved in anhydrous tetrahydrofuran (50 mL) in a reaction flask under nitrogen blanket. Phenyl magnesium bromide (1.0 mL of a 3M4 ether solution) was added dropwise while cooling with an ice/water bath. The reaction solution was then stirred at room temperature for 30 minutes. The reaction mixture was poured into 100 grams of ice/saturated ammonium chloride solution. The layers were separated and the organic layer was concentrated by rotary evaporation. The residue was chromatographed on silica gel using a 4:1 v/v mixture of hexane and ethyl acetate as the elutant. The photochromic fractions were collected, dried by rotary evaporation yielding 0.32 grams of the desired product. An NMR spectrum showed the product to have a structure consistent with 3-(4-methoxyphenyl)-3,13-diphenyl-13-hydroxy-3H-(4,5-dihydrofurano[2,3-b]-indeno[3,2-f]-naphtho)[1,2-b]pyran.

Example 2

3,3-di(4-methoxyphenyl)-13-methyl-13-hydroxy-3H-(4,5-dihydrofurano[2,3-b]-indeno[3,2-f]-naphtho)[1,2-b]pyran was obtained by following the process of Example 1, replacing 1-(4-methoxyphenyl)-1-phenyl-2-propyn-1-ol with 1,1-di(4-methoxyphenyl)-2-propyn-1-ol in Step 6, and replacing phenyl magnesium bromide with methyl magnesium iodide in Step 7. The structure was confirmed by a NMR spectrum.

Example 3

3,3-di(4-methoxyphenyl)-13-ethyl-13-hydroxy-3H-(4,5-dihydrofurano[2,3-b]-indeno[3,2-f]-naphtho)[1,2-b]pyran was obtained by following the process of Example 1, replacing 1-(4-methoxyphenyl)-1-phenyl-2-propyn-1-ol with 1,1-di(4-methoxyphenyl)-2-propyn-1-ol in Step 6, and replacing phenyl magnesium bromide with ethyl magnesium bromide in Step 7. The structure was confirmed by a NMR spectrum.

Example 4

3,3-di(4-methoxyphenyl)-13-phenyl-13-hydroxy-3H-(4,5-dihydrofurano[2,3-b]-indeno[3,2-f]-naphtho)[1,2-b]pyran was obtained by following the process of Example 1, and replacing 1-(4-methoxyphenyl)-1-phenyl-2-propyn-1-ol with 1,1-di(4-methoxyphenyl)-2-propyn-1-ol in Step 6. The structure was confirmed by a NMR spectrum.

Photochromic Property Measurement:

Each of the invention compounds is dissolved in chloroform at a concentration of 0.1%. The UV-visible absorptions (optical path of 1 cm) are then measured before and after exposure to a 365 nm UV source for 1 minutes. The photochromic properties: $\lambda_{UV}$ (absorption wavelength closet to visible spectrum before activated), $\lambda$max of the two principle absorption bands, and relative induced optical intensity, RIOD, (intensity ratio between band 1 and band 2) of these compounds are compared with corresponding compounds of prior arts as in Tables 1, 2, and 3 below.

TABLE 1

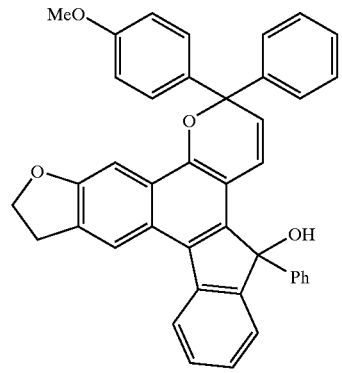

Example 1

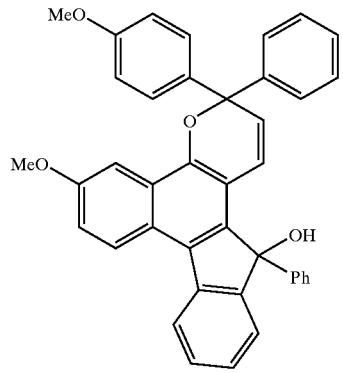

Example 5
U.S. Pat. No. 6,146,554

| Compound | $\lambda_{UV}$(nm) | $\lambda_{Vis,1}$(nm) | $\lambda_{Vis,2}$(nm) | RIOD | Solvent |
|---|---|---|---|---|---|
| Example 1 | 405 | 440 | 573 | 1.01 | Chloroform |
| Example 5 U.S. Pat. No. 6,146,554 | 400 | 445~450 | 575 | 0.88 | Transhade-150 |

TABLE 2

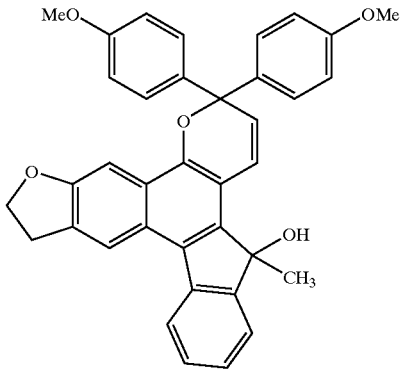

Example 2

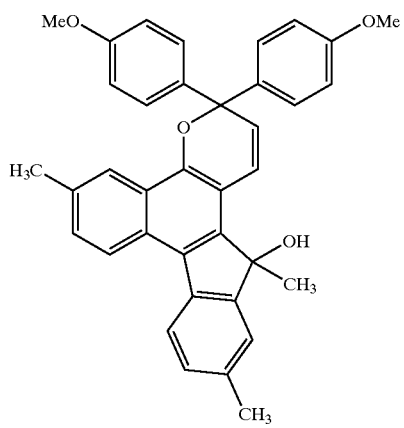

Example V2
U.S. Pat. No. 6,146,554

| Compound | $\lambda_{UV}$(nm) | $\lambda_{Vis,1}$(nm) | $\lambda_{Vis,2}$(nm) | RIOD | Solvent |
|---|---|---|---|---|---|
| Example 2 | 400 | 450 | 580 | 1.01 | Chloroform |
| Example V2 U.S. Pat. No. 6,146,554 | 359, 375 (shoulder) | 438 | 570 | 0.79 | Transhade-150 |

TABLE 3

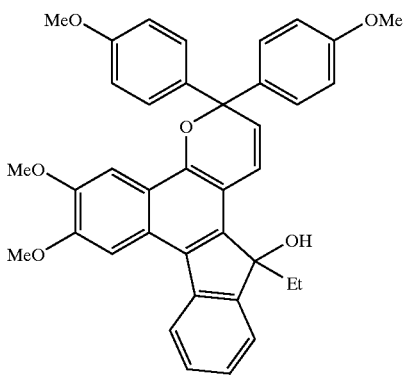

Example 5
U.S. Pat. No. 6,296,785

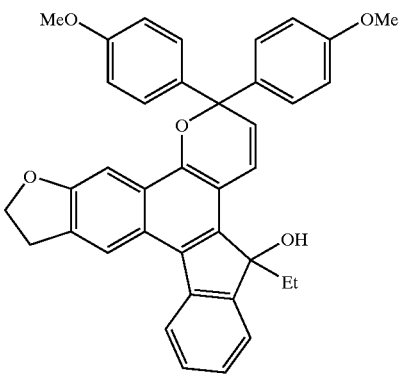

Example 3

| Compound | $\lambda_{UV}$(nm) | $\lambda_{Vis,1}$(nm) | $\lambda_{Vis,2}$(nm) | RIOD | Solvent |
|---|---|---|---|---|---|
| Example 3 | 405 | 450 | 576 | 1.00 | Chloroform |
| Example 5 U.S. Pat. No. 6,296,785 | | 458 | 584 | 1.55 | CR-307 |

In Table 4, Example 4 of the invention is used to show that the relative induced optical intensity does not vary significantly in different solvents.

TABLE 4

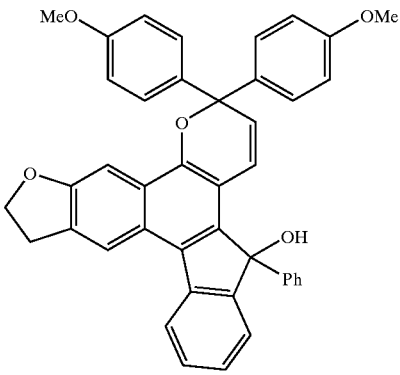

Example 4

| Solvent | $\lambda_{Vis,1}$(nm) | $\lambda_{Vis,2}$(nm) | RIOD |
|---|---|---|---|
| Acetone | 450 | 578 | 1.01 |
| Chloroform | 450 | 576 | 1.00 |
| CR-39 | 452 | 580 | 1.00 |
| Urethane | 442 | 573 | 1.02 |

It is thus demonstrated by these measurements that the naphthopyrans of the invention have two distinct absorption peaks, their bands cover majority of the visible spectrum. They display high intensity when activated by solar radiation. Relative intensity between the two bands stays close to unity regardless the substituent groups and solvents. In addition, it has been observed that they exhibit high sensitivity to solar radiation due to high UV λmax.

What is claimed is:

1. A photochromic naphthopyran having a central nucleus of the formula:

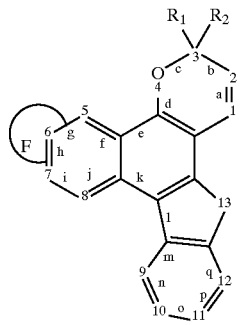

wherein F is a dihydrofuran group fused to the g, h, or i side;

$R_1$ and $R_2$ are the atoms or groups providing photochromic properties to the naphthopyran.

2. The photochromic naphthopyran of claim 1 wherein $R_1$ and $R_2$ are selected from the group consisting of aliphatic groups, aromatic groups, and heterocyclic groups.

3. The photochromic naphthopyran of claim 1 wherein $R_1$ and $R_2$ are selected from the group consisting of alkyl groups, aromatic groups, and heterocyclic groups.

4. The photochromic naphthopyran of claim 1 wherein $R_1$ and $R_2$ are selected from alkyl groups, phenyl groups, and naphthyl groups.

5. A photochromic naphthopyran having a central nucleus of the formula:

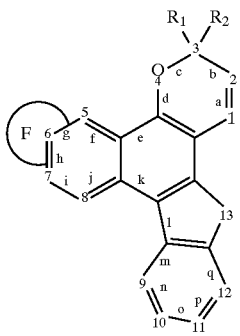

wherein F is a dihydrofuran group fused to the g, h, or i side;

$R_1$ and $R_2$ are the atoms or groups providing photochromic properties to the naphthopyran, and the 13-position may be substituted wherein the 13-position has substituents $R_3$ and $R_4$, wherein $R_3$ and $R_4$ individually represent a hydrogen atom, a hydroxy group, a halogen atom, a linear, branched, or cyclic C1–C6 alkyl, alkenyl, or alkynyl group, a linear, branched, or cyclic C1–C6 alkoxy or alkenoxy group,

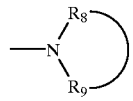

an amino group:

in which $R_8$ and $R_9$, which are the same or different, independently representing a hydrogen, a linear, branched, or cyclic alkyl group comprising 1 to 6 carbon atoms, an aryl or heteroaryl group, or representing (together with the nitrogen atom to which they are bound) a 5- to 7-membered ring which can comprise at least one other heteroatom selected from oxygen, sulfur and nitrogen, said nitrogen being optionally substituted with an $R_{10}$ group, which is a linear or branched alkyl group comprising 1 to 6 carbon atoms, a phenyl, a benzyl, or a naphthyl, an aryl or heteroaryl group selected from the group consisting of phenyl, naphthyl, phenanthryl, pyrenyl, quinolyl, isoquinolyl, benzofuranyl, thienyl, benzothienyl, dibenzofuranyl, dibenzothienyl, carbazolyl, indolyl, a mono-substituted phenyl having a substituent at the para position that is a linking group, —(CH$_2$)$_t$— or —O—(CH$_2$)$_t$—, wherein t is the integer 1, 2, 3, 4, 5 or 6, connected to an aryl group, which is a member of another photochromic naphthopyran, an aralkyl or heteroaralkyl group, the alkyl part of which is linear or branched, comprising 1 to 4 carbon atoms, a —C(O)R$_{11}$, —OC(O)R$_{11}$, or COOR$_{11}$ group, wherein $R_{11}$ is hydrogen, hydroxy, linear or branched C1–C6 alkyl, linear or branched C1–C6 alkoxy, phenyl, mono-substituted phenyl, naphthyl, mono-substituted naphthyl, amino, mono(C1–C6) alkylamino or di(C1–C6) alkylamino, e.g., N,N-dimethyl amino, N-methyl-N-propyl amino, morpholino, piperidino or pyrrolidyl, said amino substituents being selected from the group consisting of C1–C6 alkyl, phenyl, benzyl and naphthyl, and said benzyl and phenyl substituents being C1–C6 alkyl or C1–C6 alkoxy, a group —OR$_{12}$, wherein $R_{12}$ is a C1–C6 acyl, an aralkyl or heteroaralkyl group with a C1–C3 alkyl portion, a (C3–C7)cycloalkyl group, a (C2–C4)alkyl group, or $R_{12}$ is the group, —CH(R$_{13}$)R$_{14}$, wherein $R_{13}$ is hydrogen or C1–C3 alkyl and $R_{14}$ is —CN, —CF$_3$, or —COOR$_{15}$, wherein $R_{15}$ is hydrogen or linear, branched, or cyclic alkyl, aralkyl or heteroaralkyl, a group —CH(R$_{16}$)$_2$ wherein $R_{16}$ is —CN or —COOR$_{15}$, a group CH(R$_{15}$)R$_{17}$, wherein $R_{17}$ is —COOR$_{11}$, —C(O)R$_{18}$ or —CH$_2$OR$_{19}$, wherein $R_{18}$ is hydrogen, linear, branched, or cyclo-alkyl, aryl groups, amino group of formula

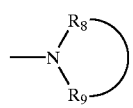

$R_{19}$ is hydrogen, —C(O)R$_{11}$, alkyl, alkoxyalkyl, phenylalkyl, mono-alkoxy substituted phenyl-alkyl, or aryl groups, a polyether, polyamide, polycarbonate, polycarbamate, polyurea, polyester residue, or a group ended by a polymerizable residue;

or $R_3$ and $R_4$ may together form a 3- to 7-member spiro-cyclic ring which can comprise at least one heteroatom selected from oxygen, sulfur, and nitrogen.

6. The photochromic naphthopyran of claim 5 wherein, (a) in the 5- and/or 8-position, a group $R_6$ is present wherein $R_6$ represents a hydrogen, a halogen, a linear or branched alkyl group which comprises 1 to 12 carbon, a cycloalkyl group comprising 3 to 12 carbon atoms, a linear or branched alkoxy group comprising 1 to 12 carbon atoms, a haloalkyl, halocycloalkyl, or haloalkoxy group corresponding to the alkyl, cycloalkyl, alkoxy groups above respectively, which are substituted with at least one halogen atom, a linear or branched alkenyl or alkynyl group comprising 1–12 carbon atoms, a linear or branched alkenoxy or alkynoxy group comprising 1–12 carbon atoms, an aryl or heteroaryl group having the same definition as that given above for aryl or heteroaryl groups within the definitions of $R_3$, $R_4$, an aralkyl or heteroaralkyl group, the alkyl group, which is linear or branched, comprising 1 to 4 carbon atoms, and the aryl and heteroaryl groups having the same definitions as those given above for $R_3$, $R_4$, an amine or amide group: $-NH_2$, $-NHR_8$, $-CONH_2$, $-CONHR_8$,

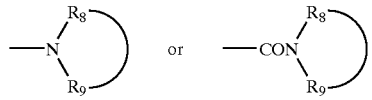

$R_8$, and $R_9$ having their respective definitions given for the amine substituents of the values $R_3$, $R_4$, a $-C(R_{15})_2R_{11,\ -OCOR15}$, or $COOR_{15}$ group, wherein $R_{11}$ and $R_{15}$ are defined supra in $R_3$ and $R_4$, a methacryloyl group or an acryloyl group,

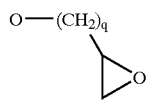

an epoxy group having the formula, in which q=1, 2 or 3, a polyether, polyamide, polycarbonate, polycarbamate, polyurea or polyester residue, or a group with polymerizable residue, (b) in the 9-, 10-, 11-, and 12-positions there are at most 4 $R_5$ groups, each being the same as $R_6$, defined hereinbefore; or (c) two adjacent $R_5$ together form a 5- to 7-member aromatic or non-aromatic ring which can comprise at least one heteroatom selected from oxygen, sulfur, and nitrogen, and/or at least one substituent selected from the group consisting of a C1 to C6 alkyl group which is linear, branched, or cyclic, a C1 to C6 alkoxy group which is linear or branched, and an amine group of formula $-NH_2$, $NHR_8$, or

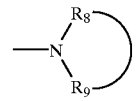

as defined in $R_3$ and $R_4$ for amine groups, said aromatic or non-aromatic ring can be optionally annelated with a benzene group.

7. The photochromic naphthopyran of claim 6 wherein $R_1$ and/or $R_2$ represent a para-substituted phenyl group, said substituents on the para-substituted phenyl group selected from hydrogen, alkyl, alkoxy, dialkylamino, diarylamino, or $R_1$ and $R_2$ together form an adamantyl group or norbornyl group or anthracenylidene group.

8. A photochromic article comprising a polymeric layer containing a photochromic amount of a photochromic naphthopyran according to claim 1.

9. A photochromic article comprising a polymeric layer containing a photochromic amount of a photochromic naphthopyran comprising 3-phenyl-3-4-methoxyphenyl)-13,13-diethyl-3H-(4,5-dihydrofurano[2,3-b]-indeno[3,2-f]-naphtho)[1,2-b]pyran.

10. A photochromic article comprising a polymeric layer containing a photochromic amount of a photochromic naphthopyran according to claim 3.

11. A photochromic article comprising a polymeric layer containing a photochromic amount of a photochromic naphthopyran according to claim 4.

12. A photochromic article comprising a polymeric layer containing a photochromic amount of a photochromic naphthopyran according to claim 5.

13. A photochromic article comprising a polymeric layer containing a photochromic amount of a photochromic naphthopyran according to claim 6.

14. A photochromic article comprising a polymeric layer containing a photochromic amount of a photochromic naphthopyran according to claim 7.

* * * * *